(12) United States Patent
Römisch et al.

(10) Patent No.: US 6,573,056 B2
(45) Date of Patent: Jun. 3, 2003

(54) PROCESS FOR PURIFYING FACTOR VII AND ACTIVATED FACTOR VII

(75) Inventors: Jürgen Römisch, Marburg (DE);
Hans-Arnold Stöhr, Wetter (DE);
Annette Feussner, Marburg (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/768,294

(22) Filed: Jan. 25, 2001

(65) Prior Publication Data

US 2001/0007901 A1 Jul. 12, 2001

Related U.S. Application Data

(63) Continuation of application No. 08/731,577, filed on Oct. 16, 1996, now abandoned.

(30) Foreign Application Priority Data

Oct. 18, 1995 (DE) .......................................... 195 38 715

(51) Int. Cl.$^7$ ...................... G01N 33/53; G01N 33/537; C12Q 1/56
(52) U.S. Cl. .......................... 435/7.1; 435/7.92; 435/13
(58) Field of Search ................................. 435/7.1, 7.92, 435/13

(56) References Cited

U.S. PATENT DOCUMENTS

| | | |
|---|---|---|
| 3,880,714 A | 4/1975 | Babson |
| 4,415,559 A | 11/1983 | Suzuki et al. |
| 4,416,812 A | 11/1983 | Becker et al. |
| 4,456,591 A | 6/1984 | Thomas |
| 5,017,556 A | 5/1991 | O'Brien et al. |
| 5,093,237 A | 3/1992 | Enomoto |
| 5,118,614 A | 6/1992 | Rybák et al. |
| 5,344,918 A | 9/1994 | Dazey et al. |
| 5,348,942 A * | 9/1994 | Little et al. |
| 5,374,617 A | 12/1994 | Morrissey et al. |
| 5,472,850 A | 12/1995 | Morrissey |

FOREIGN PATENT DOCUMENTS

| | | |
|---|---|---|
| CA | 2045869 | 12/1991 |
| EP | 0 346 241 A | 12/1989 |
| EP | 0 464 533 A | 1/1992 |
| EP | 0 547 932 A | 6/1993 |
| WO | WO 92/18870 | 10/1992 |
| WO | WO 94/22905 | 10/1994 |

OTHER PUBLICATIONS

H.C. Godal et al., "Progressive Inactivation of Purified Factor VII by Heparin and Antithrombin III," *Thrombosis Research*, vol. 5, pp. 773–775 (1974).

U. Seligsohn et al., "Coupled Amidolytic Assay For Factor VII: Its Use With A Clotting Assay to Determine the Activity State of Factor VI," *Blood*, vol. 52, No. 5, pp. 978–988 (1978).

L. Rao et al., "Affinity Purification of Human Brain Tissue Factor Utilizing Factor VII Bound to Immobilized Anti–Factor VII," *Chemical Abstracts*, Abs. No. 194493, vol. 107, No. 21, (Nov. 23, 1987).

S. Kang et al., "Purification of Human Brain Tissue Factor," *Thrombosis and Haemostasis*, vol. 59(3), pp. 400–403 (1988).

S. Kitchen et al., "A Method for the Determination of Activated Factor VII Using Bovine and Rabbit Brain Thromboplastins: Demonstration of Increased Levels in Disseminated Intravascular Coagulation," *Thrombosis Research*, vol. 50(1), pp. 191–200 (1988).

P. Neuenschwander et al., "Deletion of the Membrane Anchoring Region of Tissue Factor Abolishes Autoactivation of Factor VII But Not Cofactor Function," *J .Biol. Chem.*, vol. 267, No. 20, pp. 14477–14482 (1992).

K. Kario et al., "The Strong Positive Correlation Between Factor VII Clotting Activity Using Bovine Thromboplastin and the Activated Factor VII Level," *Thrombosis and Haemostasis*, vol. 73(3), pp. 429–434 (1995).

J. Morrissey, "Tissue Factor Modulation of Factor VIIa Activity:Use in Measuring Trace Levels of Factor VIIa in Plasma," *Thrombosis and Haemostasis*, vol. 74(1), pp. 185–188 (1995).

Rao et al (Analytical Biochemistry vol. 165, pp 365–370), 1987.*

Johnstone et al (Immunochemistry in Practice $2^{nd}$Ed. pp 207–219 & 222–224), 1987.*

Jesty et al (Blood vol. 87 (6) pp 2301–2307), Mar. 1996.*

* cited by examiner

*Primary Examiner*—Mark Navarro
(74) *Attorney, Agent, or Firm*—Finnegan, Henderson, Farabow, Garrett and Dunner, L.L.P.

(57) ABSTRACT

The invention relates to a process for purifying factor VII and/or activated factor VIIa (F VII/F VIIa) by means of binding to immobilized soluble thromboplastin.

12 Claims, No Drawings

PROCESS FOR PURIFYING FACTOR VII AND ACTIVATED FACTOR VII

This is a continuation of application Ser. No. 08/731,577 filed Oct. 16, 1996, now abandoned, incorporated herein by reference.

The invention relates to a process for purifying factor VII and/or activated factor VII (F VII/F VIIa) by means of binding to immobilized soluble thromboplastin.

Coagulation factor VII (FVII) constitutes, together with thromboplastin (tissue factor, TF), the complex which initiates the extrinsic coagulation pathway. When tissue injury occurs, TF is exposed, enabling FVII and/or FVIIa to bind to its extracellular protein domain. A hydrophobic protein region anchors TF in the membrane.

In the presence of (preferably negatively charged) lipids and calcium, the physiologically active component of the FVII/FVIIa mixture, namely TF-FVIIa, efficiently activates factor X (FX). FXa in turn (together with FVa, lipids and calcium) catalyzes the generation of thrombin. The subsequent formation of fibrin ensures wound closure, inter alia.

FVII which is bound to membrane-located TF is in turn activated by autoactivation (mediated by TF-FVIIa) or by FIXa, FXa and thrombin, thereby further amplifying the cascade-like activation of the coagulation system.

Correspondingly, a deficiency of FVII can be associated with hemostatic complications such as a tendency to hemorrhages. As a coagulation factor whose synthesis to form the physiologically functional molecule depends on the presence of vitamin K, complications can correspondingly arise, for example in association with oral anticoagulation (with vitamin K antagonists) before operations; consumption coagulopathies and liver damage represent additional indications for providing FVII replacement therapy. FVIIa, on the other hand, is a constituent of activated PPSB preparations which can be used in association with acute hemorrhages. In addition to this, FVIIa possesses a so-called factor VIII-bypassing activity which is used when providing replacement therapy to hemophilliacs who are suffering, for example, from FVIII intolerance (e.g. antibodies).

FVII/FVIIa is normally concentrated from plasma or culture supernatants (in the case of recombinant preparation) using several preparation steps, a procedure which is usually associated with corresponding losses of yield. As a protein which is related both structurally and in its properties to other coagulation factors, its purification from a corresponding mixture is both difficult and elaborate. In addition to this, there is the danger, in the case of FVII, that, as the purification process becomes more elaborate, an activation (to FVIIa) will occur which (in conformity with the sought-after preparations) must be avoided. Preparations using suitable immobilized monoclonal antibodies represent examples of rapid methods. Usually, however, elution conditions are required (pH 3 –pH4) which damage the protein irreversibly. Partial denaturation results in corresponding losses of yield and can also cause the conformationally altered molecular structures to become antigenic.

The underlying object of the present invention is therefore to provide a process for the rapid and mild purification of FVII/FVIIa.

The object was achieved as follows: FVII and/or FVIIa are removed from an FVII/FVIIa-containing solution by binding them to an immobilized sTF ("soluble" thromboplastin, soluble tissue factor), unbound molecules are removed from the matrix by washing and FVII/FVIIa is subsequently eluted under mild conditions. In this context, sTF is thromboplastin which lacks the transmembrane moiety and the cytoplasmic moiety and is consequently the extracellular domain of TF.

We have found that the interaction of FVII/FVIIa with sTF can be utilized to purify FVII and/or FVIIa. Thus, whereas the "physiological" complete (lipid-binding) TF brings about autoactivation and proteolysis or feedback activation of the bound FVII by FIXa, FXa and thrombin, FVII which is bound to sTF remains unaffected (Morrissey; Thromb. Haemostas. 1995; 74:185–188).

The binding of FVII and/or FVIIa to sTF is optimized in the presence of doubly charged ions, particularly by calcium, whereas other proteins can be removed in unbound form. Accordingly, an immobilized sTF is adsorbed to a matrix, FVII and/or FVIIa are, in the presence of calcium, bound to sTF from out of a solution and unbound molecules are removed from the solid phase by washing. The elution is carried out in a mild manner using a buffer which contains a chelating agent such as citrate, oxalate, tartrate, EDTA or the like.

The sTF can be adsorbed to a solid phase by way of non-covalent bonding or be immobilized by means of covalent bonding. Suitable binding partners are conventionally prepared sTF (prepared proteolytically from complete TF), recombinantly prepared sTF or FVII/FVIIa-binding moieties (peptide regions from sTF). The sTF, or appropriate FVII-binding regions, can be coupled to substances which simplify or optimize immobilization (e.g. as a spacer function, see below).

In a preferred approach, an sTF (Fc-sTF) which is coupled to an Fc fragment is used, as described in EP 464533 (Lauffer et al). The sTF is optimally presented, and the efficiency of the purification system is increased, by, for example, binding the Fc-sTF to an anti-Fc column or to a protein A matrix or protein G matrix. Since samples which contain Fc fragments or immunoglobulins can lead to displacement of the Fc-sTF from the matrix, it is advisable to couple the Fc-sTF covalently to the matrix using known methods.

Doubly charged ions, preferably calcium, preferably in the form of $CaCl_2$, at a concentration of from 0.01 to 500 mM, particularly preferably of from 0.5 to 50 mM, are added to the FVII/FVIIa-containing solution. The solution should have a pH of from 5.0 to 10.0, preferably of from 7.0 to 9.5. This solution is brought into contact with the sTF-matrix and the matrix is washed with a buffer solution which preferably has a pH of between 7.0 and 9.5 and a calcium concentration of between 0.5 and 50 mM. Elution is effected using a solution which contains a chelating agent, preferably citrate, oxalate, tartrate, NTA, EDTA or EGTA, in concentrations of 0.1–1000 mM, preferably between 5 and 200 mM. The solution has a pH of from 5.0 to 10.0, preferably of from 5.5 to 8.5, particularly preferably of from 6.0 to 7.5.

Samples which contain activated factors can give rise to additional generation of FVIIa (possibly from the excess of factor VII which is present) and consequently to artificial results. In order to avoid this risk, antithrombin III/heparin can be added to the sample before contact with the immobilized sTF. Since FVIIa is only inhibited slowly by ATIII/Hep. at room temperature or at higher temperatures in comparison to other, potentially interfering factors (FIIa, FIXa, FXa, etc.), the latter can be blocked, without having a significant effect on the content of FVIIa, if the intention is to purify FVIIa. TF-bound FVIIa can sometimes be inhibited more efficiently by ATIII/Hep. than are the free molecules (however, without functional heparin, ATIII reacts only very slowly, in analogy with soluble FVIIa). Therefore, the heparin which is added can be neutralized with known reagents such as protamine sulfate/Polybren® prior to contact with sTF, with the subsequent procedure being as described above.

Reversible inhibitors, e.g. benzamidine, and other cofactor-dependent inhibitors which themselves, or their accelerators, can be neutralized (for example heparin-cofactor II/heparin) are also suitable for this step of the process.

The invention is explained in more detail by the following example:

EXAMPLE

Protein A-Sepharose was loaded with Fc-sTF (10 µg/50 µl of gel matrix) and equilibrated with buffer A (50 mM tris/HCl, 150 mM NaCl, 10 mM $CaCl_2$, 0.1% human albumin, pH: 8.5). FVIIa was added to 0.5 ml of a protein solution which contained FVII (15 IU/ml) to a concentration which corresponded to 5% (in a coagulation test) of the FVII activity. The solution also contained other coagulation factors such as factors II (30 IU/ml), IX (25 IU/ml) and X (30 IU/ml), as well as a number of additional plasma proteins. This solution was diluted with an equal volume of buffer A and brought into contact with the sTF-matrix in a small column. After the flow-through had passed through the column, the matrix was washed with 0.5 ml of buffer A and bound protein was subsequently eluted with buffer B (50 mM tris/HCl, 150 mM NaCl, 50 mM sodium citrate, pH 6.5), and collected.

The eluate was tested in appropriate coagulation tests and the yield of FVII/VIIa was quantified (in relation to the starting material) by its activity and also by means of ELISA. The purity of the eluate was demonstrated by SDS-PAGE.

RESULT

The yield of FVII/FVIIa was 93% by ELISA and 90% by activity, based on the starting material. Another important finding was that, once again, 5% of the FVII activity in the eluate derived from (the added) FVIIa. This demonstrates that neither of the two molecules was bound preferentially. On the other hand, the possibility can be excluded that activation of FVII to FVIIa took place during this purification step.

While neither FII, FIX nor FX was found in the eluate, they were all found (in correspondence with the starting material) in the column flow-through. The purity of the eluate, and the powerful effect in concentrating FVII/VIIa in the eluate, is clearly shown by SDS-PAGE analysis, which convincingly demonstrates the purification effect.

What is claimed is:

1. A process for purifying at least one of Factor VII and Factor VIIa comprising:
    a) immobilizing soluble thromboplastin on a solid phase;
    b) contacting the immobilized soluble thromboplastin with a solution comprising at least one of Factor VII and Factor VIIa without promoting autoactivation of FVII and wherein the pH of the solution is from about 7.0 to about 9.5;
    c) removing unbound molecules by washing with a buffer solution with a pH of about 7.0 to about 9.5; and
    d) releasing at least one of Factor VII and Factor VIIa from the solid phase with a solution having a pH range from about 5.5 to about 8.5.

2. The process according to claim 1, wherein a chelating factor is used for releasing Factor VII and Factor VIIa.

3. The process as claimed in claim 2, wherein the chelating agent is chosen from citrate, oxalate, tartrate, NTA, EDTA, and EGTA.

4. The process according to claim 2, wherein the chelating agent is added at a concentration ranging from about 0.1 nM to about 1000 nM, and which is sufficient to release Factor VII and Factor VIIa.

5. The process according to claim 1, wherein $Ca^{++}$ ions are added at a concentration ranging from about 0.01 mM to about 500 mM in association with contacting the immobilized soluble thromboplastin with a solution comprising at least one of Factor VII and Factor VIIa without promoting autoactivation of FVII.

6. The process according to claim 1, further comprising inhibiting other, interfering activated factors in the solution comprising at least one of Factor VII and Factor VIIa prior to contacting the immobilized soluble thromboplastin.

7. The process according to claim 6, wherein inhibiting other interfering activated factors is by adding antithrombin III/heparin prior to contacting the immobilized soluble thromboplastin.

8. The process according to claim 7, further comprising neutralizing the heparin with protamine sulfate.

9. The process according to claim 1, wherein the soluble thromboplastin is non-covalently bound to the solid phase.

10. The process according to claim 1, wherein the soluble thromboplastin is covalently bonded to the solid phase.

11. The process according to claim 1, wherein the soluble thromboplastin is coupled to an Fc fragment.

12. The process according to claim 1, wherein the solution in step (d) has a pH range from about 6.0 to about 7.5.

* * * * *